United States Patent [19]
Gordon

[11] 3,934,587
[45] Jan. 27, 1976

[54] DISPOSABLE ARTICLES HAVING A WATER-PERMEABLE AND WATER-REPELLENT SURFACE

[76] Inventor: Roy Gerald Gordon, 22 Highland St., Cambridge, Mass. 02138

[22] Filed: June 17, 1974

[21] Appl. No.: 479,636

[52] U.S. Cl.......... 128/284; 128/132 D; 128/290 P; 260/112 R; 260/117; 260/78 R; 260/123.7; 260/73 R; 260/119; 428/913; 428/524; 428/530; 428/528; 428/527; 428/327; 162/9; 229/1.5; 229/3.1; 229/53; 8/116.4; 8/120
[51] Int. Cl.²................ A61F 13/16; B32B 27/42
[58] Field of Search....... 260/73, 112 R, 117, 123.7, 260/78 R; 128/283, 286, 290 P; 161/257, 263; 428/524, 527, 530, 528; 8/116.4, 120; 162/9

[56] References Cited
UNITED STATES PATENTS

| | | | |
|---|---|---|---|
| 2,471,497 | 5/1949 | Roberts et al. | 260/73 L X |
| 2,512,195 | 6/1950 | Bener | 8/116.3 |
| 3,089,493 | 5/1963 | Gaundo | 128/283 |
| 3,137,540 | 6/1964 | Osugi et al. | 260/73 L |
| 3,626,943 | 12/1971 | Worcester | 128/286 |
| 3,661,695 | 5/1972 | Berliner | 161/254 X |
| 3,799,167 | 3/1974 | Miller et al. | 128/287 |

OTHER PUBLICATIONS

B.C.M. Dorset, "Vap. Treatment for Cotton Fab.," Textile Manuf., 1969, Vol. 95, Dec. Abs.

*Primary Examiner*—George F. Lesmes
*Assistant Examiner*—Patricia C. Ives
*Attorney, Agent, or Firm*—Thompson, Birch, Gauthier & Samuels

[57] ABSTRACT

A novel material is disclosed and a process and apparatus for making the same, which process comprises reacting one side of a solid sheet or film of a polymeric compound containing reactable hydroxyl or amine groups with a vapor phase mixture of acid chloride and aldehyde. The resulting product is water-repellent along the treated side and water-permeable along the opposite, untreated side. Also disclosed are novel disposable articles such as sanitary clothing and containers for liquids fashioned from the material made by means of the process and apparatus of the present invention.

10 Claims, 4 Drawing Figures

DISPOSABLE ARTICLES HAVING A WATER-PERMEABLE AND WATER-REPELLENT SURFACE

BACKGROUND OF INVENTION

This invention is directed to the problem of producing materials and articles which are essentially waterproof during use yet can be readily disposed of in an aqueous environment, such as by flushing in a toilet, after use is completed. Such materials are particularly desirable for the production of disposable articles of sanitary clothing, for example diapers, colostomy bags, sanitary napkins, etc. In such applications, it is hygienically undesirable to store the used article with the other refuse for commercial disposal. However, other important areas of application are disposable containers of all types, such as paper cups and paper bags, and various types of packaging, such as cardboard boxes and drums. In the latter applications where the need for on-the-spot disposibility is less acute, the property of being readily dispersed or solubilized in aqueous environments would still facilitate commercial disposal of the used products. Two general approaches to this problem have been employed in the past. One approach has been to use composite structures wherein one layer of material is waterproof and intended to be reused, for example a rubber sheet, while the second layer is water-disposable. It will be appreciated that such articles are at best partially disposable. A second approach has been to use various means for coating or impregnating a base material to impart water-repellent properties thereto. In the latter case, it has generally been found that when the amount of the coating or impregnating substance used is sufficient to impart the desired degree of water-repellency, the resulting product tends to degenerate too slowly in water and causes plugging of toilets and drains. Furthermore, these methods offer little or no opportunity to control the degree of waterrepellency of the final product.

FIELD OF INVENTION

The present invention is directed to a novel material, and a process and apparatus for producing the same, which can be used to prepare articles having any desired degree of waterrepellency during use, yet are fully disposable when use is completed.

DESCRIPTION OF PRIOR ART

U.S. Pat. No. 3,089,493 is representative of both of the features which have characterized the prior art. The patent discloses a partially-disposable colostomy bag which consists of an outer reusable bag or liner made from rubber or other waterproof material and an inner, disposable bag which is made of paper coated on the inner side with a waterproofing material such as lacquer. Correspondingly, this invention presents both of the drawbacks which have characterized the prior art. The outer rubber liner cannot be disposed of in a toilet, for example; and, the inner liner requires so thick a coating of lacquer to insure uniform waterproofing that it degenerates slowly in water and can cause plugging of drain pipes.

Other patents disclose a variety of processes which involve only the second approach of coating or impregnating. For instance, U.S. Pat. No. 3,498,527 teaches that paper board containers for liquids can be waterproofed by application of a waterproofing coating such as wax or polyethylene, and a similar method is shown in U.S. Pat. No. 2,708,645 for waterproofing paper drinking cups and in U.S. Pat. No. 3,212,697 for paper grocery sacks. In U.S. Pat. No. 3,597,313, temporary wet strength is imparted to paper by coating it with a polymeric alcohol-polymeric aldehyde reaction product.

Coating processes, by themselves, have been used to produce disposable articles of sanitary clothing. In U.S. Pat. No. 3,078,849, a disposable sanitary napkin is disclosed which consists of an adsorbent layer having a liquid-repellent backing of polyvinyl alcohol or similar material capable of initially repelling water but eventually solubilizing. The degree of water-repellency, therefore the lifetime of the napkin, is controlled by varying the thickness of the backing. U.S. Pat. No. 3,542,028 is directed to a flushable sanitary napkin consisting of a cellulosic sheet treated with a fluoropolymer coating. U.S. Pat. No. 3,559,650 teaches the preparation of a sanitary napkin having two flush-disposable sides separated by a waterproof film too thin to support itself once both faces of the napkin have disintegrated upon disposal.

Analogous to the process of coating a surface with a waterproofing substance is the concept of reacting a surface with another material so as to form a reaction product on the surface which has water-repellent properties. For example, U.S. Pat. Nos. 2,130,212 and 3,137,540 teach that materials such as polymeric alcohols may be reacted with other materials to increase their water-repellent properties. The latter patent teaches treating polyvinyl alcohol articles with an aqueous emulsion of an aldehyde to impart water-repellency thereto. U.S. Pat. No. 3,626,943 teaches that disposable diapers can be made from polyvinyl alcohol and waterproofed on one side by reaction with formaldehyde. These reaction-type coating processes suffer from many of the same drawbacks heretofore mentioned for regular coating processes. In particular, there is no way of controlling the degree of water-repellency imparted to a surface. Moreover, these processes are carried out in the aqueous phase which is cumbersome, time-consuming, and results in both-sides treatment of the sheet being processed. Although most of the processes which employ some form of in situ chemical reaction to produce a water-repellent surface are carried out in the liquid phase, some vapor phase treatments are taught by U.S. Pat. Nos. 2,306,222; 2,961,338; and 3,017,290. However, this group of patents is not directed to resolving the conflicting goals of obtaining a product which is water-repellent in use but water-permeable at the time of disposal. In fact, U.S. Pat. No. 2,306,222 states that paper treated according to the invention will not disintegrate in water.

OBJECTS OF INVENTION

It is, therefore, one object of the present invention to provide a material uniquely characterized by the properties or capabilities both of being one-side water-repellent or capable of containing and storing aqueous fluids during use and of being readily other-side soluble and easily dissolved or disintegrated when disposed of in an aqueous environment.

Another object of the present invention is to provide a material wherein the degree of water-repellency exhibited during use may be easily adjusted.

Another object of the present invention is to provide a process and apparatus for producing the material of this invention.

A further object of the present invention is to provide articles suitable for sanitary clothing and as liquid-proof containers whereby they meet the ideal requirements of one-time use and of quick and easy disposal.

Further objects and advantages will become apparent as the following description proceeds.

DESCRIPTION OF PREFERRED EMBODIMENT

Figure 1:
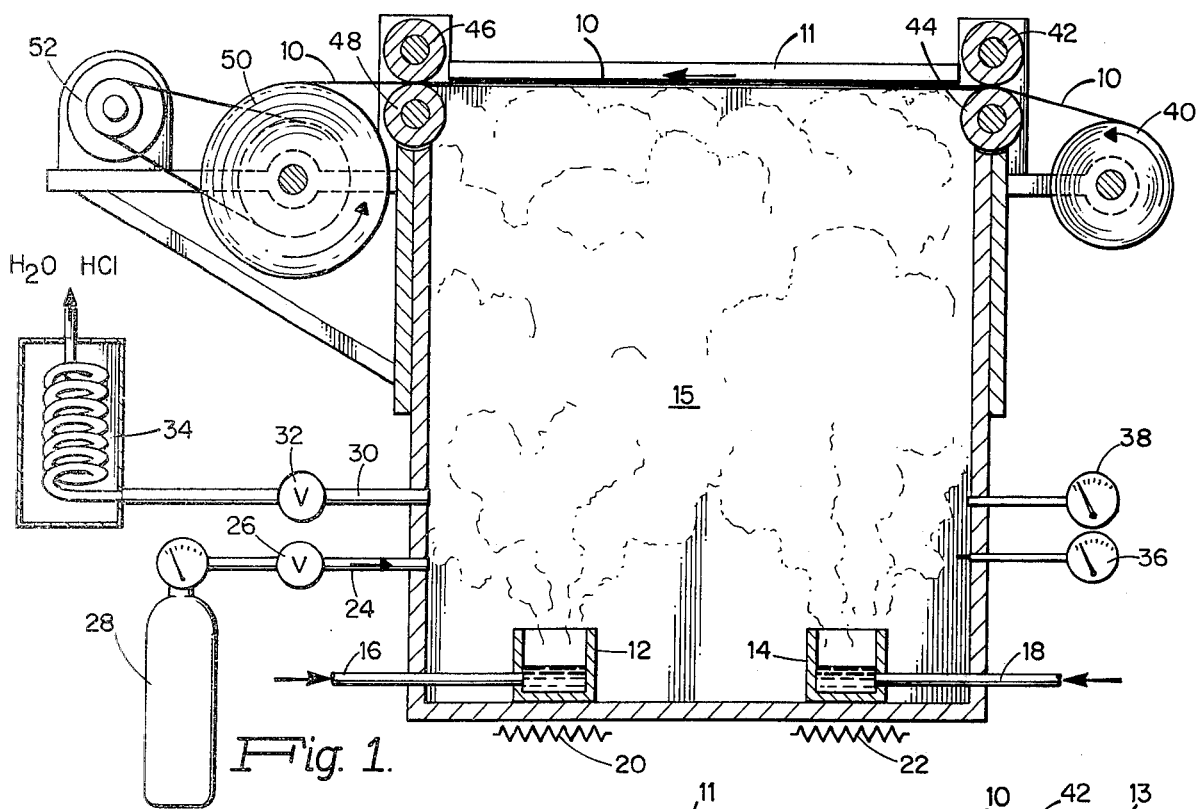
FIG. 1 is a cutaway view of the apparattus for carrying out the process of the present invention.

Referring more particularly to FIG. 1 by characters of reference, the principal element of the apparatus for practicing the present invention is an open-top rectangular reaction chamber defining an enclosed zone 15 having two liquid-holding containers or recesses 12 and 14 displaced along the bottom of the inside of said chamber. Container 12 is supplied with an acid chloride, as hereinafter described, from an external source by pipe 16. Container 14 is supplied with an aldehyde, as hereinafter described, from an external source by pipe 18. Containers 12 and 14 are independently heated by heat sources 20 and 22 respectively which are located in proximity to their respective containers. The rest of the chamber walls are also independently heated sufficiently to prevent condensation of the vapors on the interior walls. It will be appreciated that any suitable heating means may be employed.

In the practice of the present invention, acid chloride and aldehyde are fed to containers 12 and 14 respectively, and sufficient heat is applied by each of the heat sources 20 and 22 to vaporize the required amounts of acid chloride and aldehyde, thereby creating a mixed vapor having the desired molar ratio in zone 15 of the reaction chamber. In general, the useful molar ratio of acid chloride to aldehyde may vary upwards from about 1:10. The use of separate vaporizing containers eliminates any problems which could arise from the formation of acid chloridealdehyde azeotropes if the two liquids were mixed, and permits independent control of the concentration of acid chloride and aldehyde in the vapor.

The acid chlorides suitable for the practice of the present invention are those having the general formula

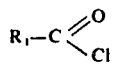

wherein $R_1$ is selected from straight or branchedchain aliphatic hydrocarbon radicals having from 1 to about 20 carbon atoms and cyclic hydrocarbon radicals having from 6 to about 20 carbon atoms. Exemplary of compounds wherein $R_1$ is selected from aliphatic hydrocarbon radicals are heptanoic acid chloride, ethyl pentanoic acid chloride, caprylyl chloride (octanoyl chloride), decanoyl chloride, lauroyl chloride, palmitoyl chloride and stearoyl chloride. Exemplary of compounds wherein $R_1$ is selected from cyclic aliphatic hydrocarbon radicals is cyclohexanecarboxylic acid chloride. In some instances it may be desirable to employ a mixture of two or more acid chlorides, and such embodiments are within the scope of the present invention. Also, acid bromides and acid iodides react in similar ways to the acid chlorides and may be substituted therefor. However, because the bromides and iodides are generally more expensive and less readily available, the equivalent acid chlorides are usually preferred. For the practice of the present invention, ordinary commercial grade acid chlorides have been found wholly suitable, the only necessary precaution being to prevent exposure of the easily hydrolyzable acid chlorides to moisture.

The aldehydes suitable for the practice of the present invention are those having the general formula

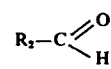

wherein $R_2$ is selected from straight or branched-chain aliphatic hydrocarbon radicals having from 1 to about 20 carbon atoms and cyclic hydrocarbon radicals having from 6 to about 20 carbon atoms. Exemplary of compounds wherein $R_2$ is selected from aliphatic hydrocarbon radicals are butanal (butyraldehyde), hexanal (caproaldehyde), ethyl-hexanal, octanal (caprylaldehye), and decanal (capraldehyde). Exemplary of compounds wherein $R_2$ is selected from cyclic hydrocarbon radicals are cyclohexyl methanal (cyclohexanecarboxaldehyde) and methyl cyclohexyl methanal. In some instances it may be desirable to employ a mixture of two or more aldehydes, and such embodiments are within the scope of the present invention. For the practice of the present invention, ordinary commercial grade aldehydes have been found wholly suitable.

An alternative to employing separate containers of acid chloride and aldehyde is to use one container or recess in the reaction chamber and one mixed feed stream, in cases for which no problem with azeotrope formation is found. One particular means of obtaining such a mixture of acid chloride and aldehyde is to begin with acid chloride and partially hydrogenate it to aldehyde using Rainey nickel or similar catalyst. Such a procedure, of course, results in a blend of acid chloride and aldehyde having the same hydrocarbon chains, but this is perfectly acceptable for the process of this invention.

The reaction chamber is also furnished with a gas inlet 24 and a valve 26 for adding diluent gas to the chamber, and similarly is furnished with an outlet 30, valve 32, and a reflux condenser 34 maintained at about 100°C, which allows reaction byproducts HCl (gas) and $H_2O$ (steam) to escape, but condenses reactant vapors and returns them to the reaction chamber. The preferred diluent gas is nitrogen which is inexpensive and does not react with aldehyde and acid chloride vapors, whereas the oxygen in air could lead to oxidation of the reactants. Nitrogen may be conveniently supplied by a cylinder 28 of the compressed gas. Ordinarily the process of the present invention is carried out at or about atmospheric pressure, i.e. about one atmosphere or 14.7 psia., and at a reactant concentration of about one-half atmosphere, i.e. a 50% dilution. However, it is also within the scope of the present invention to employ total pressures above one atmosphere, and it has been found in some instances that this will increase the speed of the reaction. Accordingly, in the preferred practice of the present invention, the reaction chamber is also furnished with an external thermometer 36 and pressure gauge 38 recording the internal conditions of the reaction chamber so that these important factors may be continuously monitored.

Affixed to one wall of the rectangular reaction chamber by suitable supporting means is a spool or roll 40 of the sheet or film 10 of polymeric compound employed in the present invention. The sheet or film may be of any suitable thickness such as about 1 mil but must be thick enough to be reasonably self-supporting and thin enough to be reasonably flexible. The apparatus may, however, be adapted to accommodate flat sheets of materials which are too stiff or brittle to be rolled on a spool, or shaped objects whose surfaces are to be made waterproof by exposure to the vapors.

The polymeric compounds which are suitable for the sheets or films of the present invention are those having a molecular weight in excess of about 1000 and containing reactable hydroxyl or amine goups in their molecular structures. The relative proportion of hydroxyl or amine groups in the polymeric structure to the rest of the polymer is not critical except that there must be a high enough proportion of these groups to render the polymeric sheet water-permeable if not water-soluble. Exemplary of suitable polymeric compounds having free hydroxyl groups (the polymeric alcohols) are polyvinyl alcohol, amylose (soluble starch), cellulose (non-soluble starch), and water-soluble cellulose ethers such as methyl cellulose wherein about 50% of the original cellulose hydroxyl groups are replaced by [—OCH$_3$] groups and ethyl cellulose wherein about one-third of the original hydroxyl groups are replaced by [—OCH$_2$CH$_3$] groups. Mixtures of two or more polymeric alcohols may also be employed. In some instances where the polymeric alcohol is too rigid and brittle, additional flexibility can be imparted thereto by the use of a plasticizer. There are many conventional plasticizers for polymeric alcohols, for example glycerin in a porportion of about 30 parts by weight glycerin to 100 parts by weight alcohol. The degree of flexibility thus imparted can be adjusted by varying the amount of plasticizer to suit particular needs. The presence of typical plasticizers in the polymeric alcohol has not been found to adversely affect the waterproofing process of this invention. Exemplary of suitable polymeric compounds having free amine groups are the polyamides such as polyacrylamide and the polypeptides such as gelatine wool.

No special preparation of the polymeric surface is necessary in practicing this invention except that the surface to be treated should be clean and free of dirt and moisture. When cleaning is necessary, dirt should be removed using non-aqueous cleansers such as chlorinated ethylene and similar "dry cleaning" solvents.

Instead of treating a sheet which consists entirely of the polymeric compound, it is also within the scope of this invention to coat cloth or paper with the polymeric compound on the side to be treated thereby forming a composite structure. This can be done, for example, by dissolving the polymeric alcohol and plasticizer in water, alcohol, or some other suitable solvent, using enough solvent to obtain a solution of the desired viscosity. The solution can then be sprayed, rolled, painted or spread by any conventional means on the surface of the paper or cloth, which is then allowed to dry. If a relatively non-porous paper or cloth is used, this results in a coating of polymeric alcohol firmly bonded to one surface, and penetrating part way into the paper or cloth. A sheet thus prepared can be waterproofed on the polymeric alcohol side, while leaving the opposite side of the sheet open to attack and solution by water.

Figure 2:
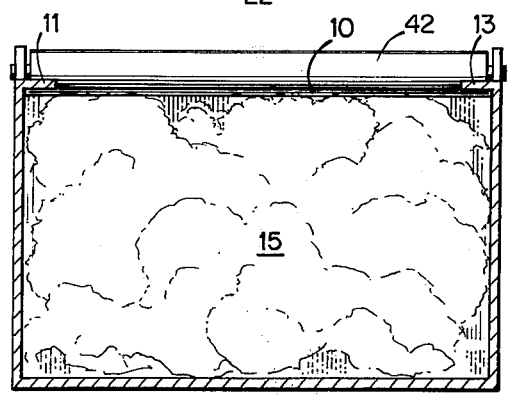
FIG. 2 is a side view taken along a section through the apparatus shown in FIG. 1.

The spool or roll 40 and the sheet 10 of polymeric material wound on the spool are very slightly less wide than the reaction chamber so that the sheet can pass between the speciallyformed lips running length-wise along both sides of the chamber. These lips 11 and 13, illustrated more clearly in FIG. 2, are seen to comprise narrow ledges projecting from the two length-wise sides of the reaction chamber and having slits at the points where they would otherwise by joined to the width-wise sidewalls of the chamber. By maintaining close tolerances between the lips and the sheet 10 of polymeric material as it is passed through the slits and under the lips, it is possible to provide an excellent seal at the open top of the reaction chamber. Although the lips could be extended width-wise so as to cover the chamber completely, it has been found that there are advantages to leaving the side of the polymeric sheet which is not to be treated exposed to the open air. First, this provides a cooling effect throughout the sheet so that vapors of acid chloride and aldehyde inside the chamber in zone 15 condense more readily on the internal surface of the sheet thereby facilitating the treatment. Also, by leaving the outer surface exposed, the likelihood of any escaped acid chloride and aldehyde vapors condensing on the untreated side is minimized.

Referring again to FIG. 1, coming off spool 40, the sheet 10 is passed between rollers 42,44 and then through the slits as described above and over the top of the reaction chamber. The mixed vapors of aldehyde and acid chloride inside the chamber react with the exposed surface of the polymeric compound to form a novel water-repellent material. At the opposite wall of the chamber, the treated sheet is removed from the chamber by passing through the second set of slits defined by lips 11,13 and between another set of rollers 46,48 and wound on a take-up spool 50 driven by variable speed motor 52. Sufficient tension is maintained between rollers 42,44 and rollers 46,48 so that a tight seal is formed between the polymeric sheet and the lips of the reaction chamber. Such a design has been found to work quite well in maintaining the vapors inside the chamber when operated at or about atmospheric pressure. Certain design changes would be required, however, to operate the reaction chamber at pressures higher or lower than atmospheric pressure.

The reaction time, that is the length of time for which it is necessary to expose the polymeric sheet to the vapors in the reaction chamber, varies according to the specific materials being employed, the reaction conditions, and the concentration of aldehyde and acid chloride in the chamber. Typically, however, the required time of exposure is about ten seconds to three minutes. The temperature and concentration of reactants in the reaction chamber may be varied to obtain a desired rate of reaction. The exposure time for a reaction chamber of a given length is easily adjusted by changing the speed of the motor 52 driving take-up spool 50. It is preferred to adjust the speed so that the surface treatment is completed by the time the sheet has traveled the length of the reaction chamber. The two interior rollers 44 and 48 will tend to remain clean of reactants because they are heated to a temperature close to that of the interior of the reaction chamber which temperature is above the boiling point of the aldehyde and acid chloride. Thus, these vapors will not generally condense on the internal metal parts of the reaction chamber. The treated sheet collected on spool 50 may then be used for a variety of novel applications as hereinafter described.

One of the principal advantages of the method of the present invention over the prior art is that it offers the opportunity to control the degree of water-repellency imparted to a surface within quite narrow ranges. As used herein, the term "waterproof" is applied to a surface which, during continuous contact with an aqueous fluid, will contain the fluid without leakage for a period of about 8 hours. The term "water-repellent" is used as a generic term to cover both waterproof surfaces, as described above, and surfaces which do not meet this criteria but demonstrate at least some ability to prevent the passage of water. The ability to control the degree of water-repellency is the result of being able to simultaneously react aldehyde and acid chloride with the polymeric surface by the vapor phase process. Although the precise nature of the resulting chemical reaction is not known, when a polyvinyl alcohol is employed as the polymeric sheet, the following is believed to represent the dependent and competing reactions which occur:

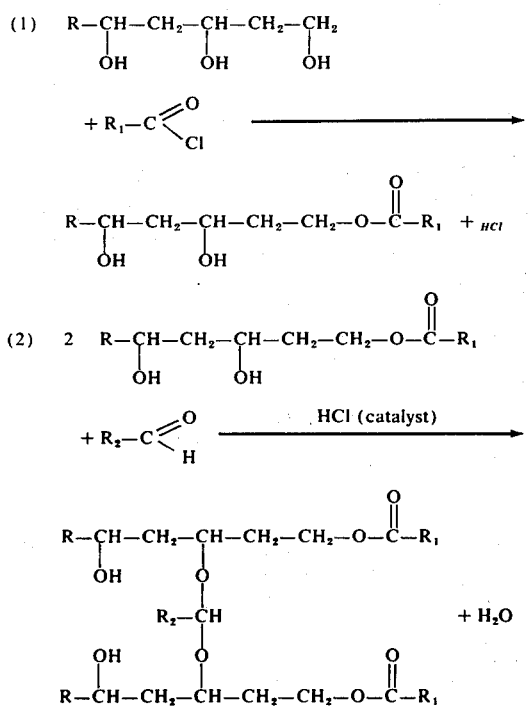

In reaction (1) above, one free hydroxyl group of polyvinyl alcohol reacts with aliphatic acid chloride to form a water-insoluble aliphatic ester and hydrogen chloride. In reaction (2) above, the hydrogen chloride formed by reaction (1) catalyzes the addition of aliphatic aldehyde to other free hydroxyl groups along the polyvinyl alcohol chain to form water-insoluble aliphatic acetals. Cross-linking between polyvinyl alcohol chains using the acetal groups as shown in reaction (2) results in a physically harder and more waterproof surface than that formed by the acid chloride reaction product alone.

The two reactions are interdependent in the sense that the addition of aliphatic aldehyde to free hydroxyl groups requires the presence of hydrogen chloride or similar catalyst, and the hydrogen chloride is introduced into the reaction chamber only as the result of the reaction between free hydroxyl groups and acid chloride. The two reactions are competing in the sense that only a limited number of reaction sites, i.e. free hydroxyl groups, are available on the polymeric surface. Thus, a high relative concentration of acid chloride to aldehyde in the vapor mixture of about 4:1 or higher promotes a relatively rapid reaction since large quantities of hydrogen chloride are quickly generated and catalyze the aldehyde reaction. On the other hand, the majority of the reaction sites on the polymeric surface are taken by ester groups, there is little acetal crosslinking, and the resulting treated surface is comparatively soft and of lesser durability. In some applications it may be desirable to use acid chloride alone to form an especially soft surface of relatively low water-repellency. If instead a relatively low concentration of acid chloride to aldehyde of about 1:2 or lower is used in the vapor mixture, the reaction is relatively slow at least until sufficient hydrogen chloride is generated to catalyze the aldehyde condensation. However, the majority of the reaction sites on the polymeric surface are taken by acetal groups, there is extensive crosslinking, and the resulting surface is physically tough, durable, and highly water-resistant for prolonged periods of time.

A third competing reaction may also occur although to a far lesser extent than the condensation of acid chloride and aldehyde. In this reaction, hydrogen chloride produced by the acid chloride condensation reacts with free hydroxyl groups to form a very much water-insoluble alkyl chloride.

Apart from the control of surface strength and water-repellency, there are additional advantages to employing the vapor phase mixture of acid chloride and aldehyde for treating the polymeric surface. Foremost in this regard is the fact that the vapor phase process of the present invention permits a oneside waterproofing treatment, the importance of which is discussed hereinafter. This, of course, is not possible with conventional liquid phase processes for waterproofing materials. Vapor phase treatment also avoids the problems of puckering and wrinkling of paper materials which have been subjected to liquid phase treatments. The vapor phase process results in a much more uniform surface since the reactants can reach even small pores and cracks in the surface of the polymeric material. From a mechanical point of view, the vapor phase process is more easily carried out than liquid phase treatment, and there is less opportunity for clogging of the apparatus. There is no need for the costly and time-consuming drying steps employed in liquid processes. There is no waste of raw materials nor any need for expensive liquid solvents. The vapor phase reaction occurs quite rapidly and is generally completed in ten seconds to about 3 minutes. Prior art liquid processes, by contrast, have generally required treatment times of about thirty minutes to an hour or more. The time factor is particularly important in making the process of the present invention economical and commercially feasible for treating paper and other low cost materials.

The use of a mixture of acid chloride and aldehyde is particularly advantageous because, as discussed above, the acid chloride reaction with free hydroxyl groups conveniently produces in situ the hydrogen chloride needed to catalyze the aldehyde condensation. It is possible to catalyze the aldehyde condensation by supplying the acid catalyst in some other way such as the introduction of dry hydrogen chloride from an external source or using aluminum trichloride vapor. However, it has been found difficult to introduce such materials and deliver them to the reaction surface in controlled amounts. Furthermore, aluminum trichloride has been found to promote the decomposition of aldehyde at elevated temperatures. In the process of the present invention, the hydrogen chloride is not only conveniently produced in situ but is produced right at the reaction surface where it is needed to catalyze the aldehyde condensation. Furthermore, the aldehyde condensation occurs only with pairs of free hydroxyl groups. Thus, the use of aldehyde alone catalyzed with an external source of catalyst leaves isolated unreacted hydroxyl groups and may result in a surface having incomplete water-repellent characteristics. By employing a combination of acid chloride and aldehyde it is possible to react virtually all of the hydroxyl groups on the surface. Finally, the raw materials for the present invention, acid chloride and aldehyde, are readily obtainable and inexpensive compared to some of the prior art waterproofing materials. Also, the waterproofed products according to the present invention are fully biodegradeable and will not cause longterm damage to the environment.

Whereas the water-repellent characteristics of polyvinyl alcohol appear to be fully developed at the conclusion of the treatment, the water-repellency of some polymeric materials such as cellulose appear to improve for several days following treatment if "aged" in a dry place at room temperature. Also it has been found that the use of longer-chain acid chlorides and aldehydes significantly improves the waterproofing properties of some polymeric materials such as cellulose. Thus, excellent results were obtained by treating paper and cotton with a vapor mixture of stearoyl chloride and stearaldehyde for about 30 seconds. On the other hand, for polyvinyl alcohol, no significant change in the waterproofing properties of the treated surface was found to result from varying the chain lengths of acid chloride and aldehyde over the range of 6, 8, 10, 12, 14 and 16-carbon atom aliphatic chains. Longer chain lengths of the reactants have been found, however, to increase the softness and the tackiness of the treated surface.

Although the benefits and advantages of the present invention as set forth above as compared to prior art materials and processes for waterproofing are substantial in and of themselves, only in the consideration of actual applications of the present invention can these by fully appreciated. The material and process of the present invention is useful in all applications requiring a surface which is waterproof or at least water-repellent for a certain period of time but is water-disposable after use. Diapers for children and other persons who are incontinent either because of old age or physical disability are one type of article for which the material and process of the present invention are ideally suited.

Figure 3:
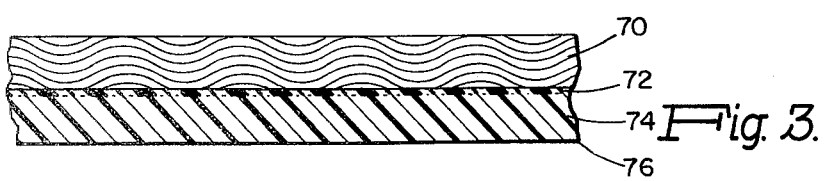
FIG. 3 is a cross section of the composite fabric for making articles of sanitary clothing according to the present invention.

Referring now to FIG. 3, what is illustrated is a cross-section of a diaper made by the process and from the material of the present invention. On the inner side of the diaper, the portion which contacts the body, is a soft layer 70 of an absorbent and water-disposable material. Suitable materials for this purpose are well-known in the art and include nonwoven rayon or cotton fibers, crepe paper, wood pulp or similar material. These are very lightly compressed to form a pad capable of absorbing and retaining a maximum amount of fluid, the individual fibers of the pad, however, being sufficiently compressed so that fluid material does not flow too freely through it. The absorbent layer 70 is bonded by suitable means to the treated surface 72 of a polymeric sheet 74 processed according to the present invention. Such bonding means include various conventional adhesives as well as the surface 72 itself which, under some process conditions, particularly high vapor pressures and using longer chain reactants, may be somewhat tacky when it is first treated with acid chloride and aldehyde. Polyvinyl alcohol sheets are especially suitable for forming into diapers and similar articles because they are easily plasticized to the desired degree of flexibility.

When in use, a diaper comprising a composite structure as shown in FIG. 3 will absorb large quantities of liquid material on the inside layer 70, yet remain perfectly dry along the outer surface 76 of the polymeric layer 74. Water-repellent surface 72 acts as a barrier to prevent seepage of the liquid through to the polymeric layer. In some applications it is desirable that the surface 72 remain completely waterproof for long periods of time such as for a day or longer. In this case, the relative proportions of acid chloride to aldehyde in the reaction chamber may be varied as described above to obtain a strong and highly waterproof surface. On the other hand, in many typical uses a diaper is designed to be changed every several hours and need not be absolutely waterproof during the interim. In fact, it is often desirable that a diaper have some capacity to "breathe," that is to withhold liquid while permitting the passage of water vapor so that the absorbent pad 70 will gradually air-dry. For such applications, cellulose-based paper is the preferred polymeric sheet, and the relative proportions of acid chloride to aldehyde in the reaction chamber may be varied as described above to obtain a surface 72 which is merely temporarily water-fepellent and will permit the passage of water vapor. Correspondingly, any intermediate degree of water-repellency or waterproofness is easily obtained. Alternatively, it will be appreciated that additional physical strength and waterproofness can be obtained by placing two or more treated paper sheets together in such a manner that each treated side except for the outermost sheet is next to the untreated side of the adjoining sheet so that the composite sheet will still be waterproof on one side yet waterpermeable from the opposite side.

Most important, however, is the fact that any diaper made according to the present invention is completely flush-disposable regardless of whether the surface 72 is a soft, water-repellent surface or a tough, waterproof surface. The reason for this novel feature is that when disposed of in an aqueous environment, the diaper is attacked from both sides and wholly disintegrates and dissolves in water. The polymeric material which comprises the outer layer 74 of the diaper is readily water-soluble because of the large number of hydrophilic groups in its molecular structure. The layer of absorbent material 70 disintegrates and flakes away leaving only a very thin waterinsoluble surface 72. Whereas the waterproof coatings of prior art patents had to be relatively thick to insure uniform and thorough waterproofing, the layer 72 in the present invention need be no thicker than a few layers of molecules. It will be appreciated that this feature of the present invention insures an article which is completely water-disposable and has no capacity whatsoever to clog or stop drains and pipes. Furthermore, the degree of water-repellency of the layer 72 of the present invention is readily adjusted as previously discussed whereas a layer of lacquer or similar material is either sufficiently thick to be wholly waterproof or too thin to be uniformly water-repellent over an entire surface.

Figure 4:
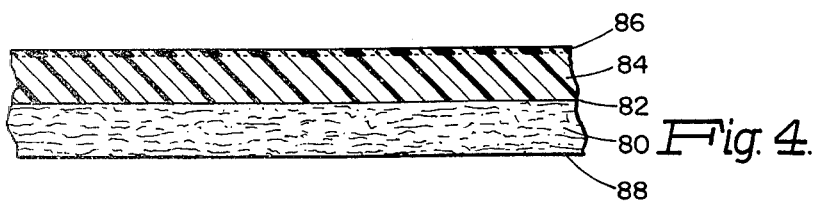
FIG. 4 is a cross section of the composite material for making paper containers according to the present invention.

FIG. 4 illustrates another type of composite structure for the making of disposable, water-repellent articles in accordance with the present invention, particularly containers for liquids such as paper drinking cups. Layer 80 is a flexible sheet of paper, cardboard or similar material which may be used in the construction of containers. Bonded to one surface 82 of the paper sheet is a layer 84 of polymeric material according to the present invention. The polymeric material is bonded to the paper sheet by any suitable means as earlier described, for example spraying, rolling or painting it on as a solution in an appropriate volatile solvent and allowing the composite sheet to dry. The surface 86 of the polymeric layer 84 is next treated with a vapor phase mixture of acid chloride and aldehyde according to the present invention, to impart water-repellent properties thereto. The treated composite sheet can then be fashioned into useful articles such as drinking cups, garbage bags, bed-pan liners and cartons wherein the treated, water-repellent surface 86 is used as the inner surface, i.e. the surface which ordinarily comes into contact with a liquid when the article is in use. Again depending on the particular application, the strength and degree of waterproofness or water-repellency of the composite sheet may be readily varied as necessary by the process of this invention. When such an article is discarded and disposed of in an aqueous environment, water attacks the article through its outer surface 88 flaking away and disintegrating the paper or cardboard fibers in layer 80 and then dissolving the water-soluble polymeric layer 84 leaving only a molecular layer 86 of waterinsoluble material. This layer is too thin to support itself and is readily broken up and carried away by a water stream such as in a flush toilet.

EXAMPLE 1

A sheet of polyvinyl alcohol was treated with a vapor phase mixture of octanoyl chloride, $CH_3(CH_2)_6COCl$, and octanal, $CH_3(CH_2)_6CHO$, at 280°F for 20 seconds. The relative proportion of acid chloride to aldehyde was about 3:7, and the total vapor pressure of the reactants was ½ atmosphere. The resulting treated surface was tough, durable and remained waterproof for a period of greater than 24 hours when tested by placing the treated sheet over an open vessel with a small amount of water on top and watching for the first signs of leakage through the untreated underside.

EXAMPLE 2

The process of Example 1 was repeated using a 4:6 mixture of lauroyl chloride, $CH_3(CH_2)_{10}COCl$, and dodecanal, $CH_3(CH_2)_{10}CHO$, at a total vapor pressure of the reactants of ½ atmosphere. The treatment time was 40 seconds at 400°F, and the result was a tough, durable, waterproof surface.

EXAMPLE 3

The process of Example 1 was repeated using an 8.5:1.5 proportion of octanoyl chloride, $CH_3(CH_2)_6COCl$ and dodecanal, $CH_3(CH_2)_{10}CHO$, at 300°F for 1 minute. The resulting treated surface demonstrated a considerably lesser tensile strength than did the surfaces of Examples 1 and 2 above, but remained waterproof for a period of 8 hours.

EXAMPLE 4

Cellulose paper sheets ("onionskin" thin typing paper, and thin "parchment" tracing paper) were treated in separate tests with stearaldehyde and/or stearoyl chloride vapors respectively at about 440°F for 30 seconds. The treated sheets were waterrepellent on the treated side, but water was readily absorbed through the untreated side so as to disperse the paper fibers and disintegrate the sheets. A particular advantage of the products of this example is that the fibrous paper sheets are somewhat permeable to water vapor, allowing diapers fashioned therefrom to "breathe," while still containing liquid water effectively.

Although several embodiments of the present invention have been described and illustrated, it will be apparent to those skilled in the art that various changes and modifications may be made therein without departing from the spirit of the invention or from the scope of the appended claims.

Having described the invention, what is claimed is:

1. An article of manufacture comprising a thin sheet, one side of said sheet being water-permeable and the other side being water-repellent, wherein said water-permeable side comprises a polymeric compound having a molecular weight in excess of about 1000 and having free hydrophilic groups selected from hydroxyl and amine groups and said water-repellent side comprises the reaction product of said polymeric compound with a vapor phase mixture comprising acid chloride having the general formula

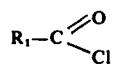

and aldehyde having the general formula

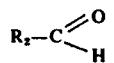

wherein $R_1$ and $R_2$ are independently selected from straight or branched-chain aliphatic hydrocarbon radicals having from 1 to about 20 carbon atoms and cyclic hydrocarbon radicals having from 6 to about 20 carbon atoms, further wherein the molar proportion of acid chloride to aldehyde in the vapor phase mixture is greater than about 1:10.

2. An article of manufacture according to claim 1 wherein said reaction is carried out at atmospheric pressure and at a temperature which is both high enough to create a vapor pressure of acid chloride and aldehyde in the vapor phase of about one-half atmosphere and to heat the polymeric compound to the temperature required for reaction to occur.

3. An article of manufacture according to claim 1 wherein said solid phase polymeric compound is polyvinyl alcohol having a molecular weight greater than about 1000.

4. An article of manufacture according to claim 1 wherein said vapor phase mixture comprises about 30 mol-% octanoyl chloride and about 70 mol-% octanal.

5. An article of manufacture according to claim 1 wherein said vapor phase mixture comprises about 85 mol-% octanoyl chloride and 15 mol-% dodecanal.

6. An article of manufacture according to claim 1 wherein said polymeric compound is exposed to said vapor phase mixture for a period of about 10 seconds to 3 minutes.

7. A disposable paper container for containing aqueous liquids comprising cellulosic paper which has been exposed along the side normally coming into contact with aqueous liquids to a vapor phase mixture comprising acid chloride having the general formula

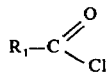

and aldehyde having the general formula

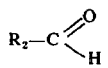

wherein $R_1$ and $R_2$ are independently selected from straight or branched-chain aliphatic hydrocarbon radicals having from 1 to about 20 carbon atoms and cyclic hydrocarbon radicals having from 6 to about 20 carbon atoms, further wherein the molar proportion of acid chloride to aldehyde in the vapor phase mixture is greater than about 1:10.

8. A disposable paper container for containing aqueous liquids comprising paper having a film on one side formed by contact with polyvinyl alcohol and subsequently exposed along said polyvinyl alcohol side to a vapor phase mixture comprising acid chloride having the generaal formula

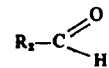

and aldehyde having the general formula

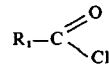

wherein $R_1$ and $R_2$ are independently selected from straight or branched-chain aliphatic hydrocarbon radicals having from 1 to about 20 carbon atoms and cyclic hydrocarbon radicals having from 6 to about 20 carbon atoms, further wherein the molar proportion of acid chloride to aldehyde in the vapor phase mixture is greater than about 1:10.

9. A disposable article of sanitary clothing comprising a sheet of polyvinyl alcohol treated along the body-facing side by exposure to a vapor phase mixture comprising acid chloride having the general formula

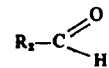

and aldehyde having the general formula

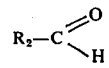

wherein $R_1$ and $R_2$ are independently selected from straight or branched-chain aliphatic hydrocarbon radicals having from 1 to about 20 carbon atoms and cyclic hydrocarbon radicals having from 6 to about 20 carbon atoms, further wherein the molar porportion of acid chloride to aldehyde in the vapor phase mixture is greater than about 1:10, and bonded to said sheet along said treated side a soft, absorbent layer of a water-disposable material.

10. A disposable article of sanitary clothing according to claim 9 wherein said article is suitable for use as a diaper.

* * * * *

UNITED STATES PATENT AND TRADEMARK OFFICE
CERTIFICATE OF CORRECTION

PATENT NO. : 3,934,587
DATED : January 27, 1976
INVENTOR(S) : Roy Gerald Gordon

It is certified that error appears in the above-identified patent and that said Letters Patent are hereby corrected as shown below:

Col. 3, line 10 - "apparattus" should be -- apparatus --.

Col. 3, line 61 - "branchedchain" should be -- branched-chain --.

Col. 4, lines 30-31 - "(caprylaldehye)" should be -- (caprylaldehyde) --.

Col. 5, line 43 - "porpotion" should be -- proportion --.

Col. 5, line 52 - after "gelatin" insert -- and --.

Col. 6, line 12 - "speciallyformed" should be -- specially-formed --.

Col. 10, line 45 - "fepellent" should be -- repellent --.

Col. 10, line 67 - "waterinsoluble" should be -- water-insoluble --.

Col. 12, line 16 - "waterrepellent" should be -- water-repellent --.

Claim 8, col. 13, line 43 - "generaal" should be -- general --.

Signed and Sealed this twenty-seventh Day of April 1976

[SEAL]

Attest:

RUTH C. MASON
Attesting Officer

C. MARSHALL DANN
Commissioner of Patents and Trademarks